United States Patent
Campbell et al.

(10) Patent No.: US 7,345,177 B2
(45) Date of Patent: Mar. 18, 2008

(54) VAPOR PHASE CATALYTIC CHLORINATION OF β-PICOLINE

(75) Inventors: Kent Douglas Campbell, Concord, CA (US); Dana Alan Livingston, Clayton, CA (US); Hawk Suewah Wan, Antioch, CA (US); Kenneth Michael Larson, Walnut Creek, CA (US); Brian John Schoeman, Midland, MI (US); Steven Roy Lakso, Shepherd, MI (US)

(73) Assignee: Dow AgroSciences LLC, Indianapolis, IN (US)

(*) Notice: Subject to any disclaimer, the term of this patent is extended or adjusted under 35 U.S.C. 154(b) by 233 days.

(21) Appl. No.: 11/114,831

(22) Filed: Apr. 26, 2005

(65) Prior Publication Data

US 2005/0240024 A1     Oct. 27, 2005

(51) Int. Cl.
*C07D 211/72*     (2006.01)

(52) U.S. Cl. ..................................................... 546/345

(58) Field of Classification Search ................. 546/345
See application file for complete search history.

(56) References Cited

U.S. PATENT DOCUMENTS

| | | | |
|---|---|---|---|
| 3,370,062 A | | 2/1968 | Corran |
| 3,420,833 A | | 1/1969 | Taplin |
| 4,205,175 A | | 5/1980 | Bowden et al. |
| 4,241,213 A | * | 12/1980 | Nishiyama et al. ......... 546/345 |
| 4,288,599 A | | 9/1981 | Nishiyama et al. |
| 4,324,627 A | | 4/1982 | Cartwright |
| 4,429,132 A | * | 1/1984 | Whittaker ................... 546/346 |
| 4,483,993 A | | 11/1984 | Marinak et al. |
| 4,497,955 A | | 2/1985 | Marinak et al. |
| 5,247,093 A | | 9/1993 | Toomey |

* cited by examiner

*Primary Examiner*—Janet L. Andres
*Assistant Examiner*—Binta Robinson
(74) *Attorney, Agent, or Firm*—Craig Mixan

(57) ABSTRACT

2-Chloro-5-trichloromethylpyridine is obtained by chlorinating β-picoline in the vapor phase using a Mordenite zeolite or a supported palladium catalyst.

3 Claims, No Drawings

VAPOR PHASE CATALYTIC CHLORINATION OF β-PICOLINE

FIELD OF THE INVENTION

The present invention concerns a process for the manufacture of 2-chloro-5-trichloromethylpyridine. More particularly, the present invention concerns a process for the manufacture of 2-chloro-5-trichloromethylpyridine by the selective vapor phase chlorination of β-picoline in the presence of a catalyst. The catalyst is selected from the group consisting of a dealuminated Mordenite zeolite or a supported palladium catalyst.

BACKGROUND OF THE INVENTION

2-Chloro-5-trichloromethylpyridine (β-2-tet) is a key intermediate for the production of several agricultural chemicals including, for example, fluazifop, haloxyfop, fluazuron and fluazinam. However, β-2-tet is difficult to obtain by direct chlorination of β-picoline. U.S. Pat. Nos. 3,370,062 and 3,420,833 describe the uncatalyzed vapor phase chlorination of picolines in general. The uncatalyzed vapor phase chlorination of β-picoline is described in U.S. Pat. Nos. 4,205,175, 4,241,213 and 5,247,093. U.S. Pat. No. 4,288,599 describes the the sequential chlorination and fluorination of β-picoline in the vapor phase. U.S. Pat. No. 4,429,132 describes the vapor phase chlorination of β-picoline in the presence of a metal oxide or a metal halide catalyst. The uncatalyzed liquid phase chlorination of β-picoline is described in U.S. Pat. Nos. 4,483,993 and 4,497,955 and the ultraviolet catalyzed liquid phase chlorination of β-picoline is described in U.S. Pat. No. 4,324,627. However, none of these processes provide β-2-tet in good yield at high conversion of β-picoline.

Because of the difficulty in obtaining β-2-tet by direct chlorination of β-picoline, it would be desirable to have a direct chlorination process with improved selectivity to β-2-tet.

SUMMARY OF THE INVENTION

It has now been found that the amount of 2-chloro-5-trichloromethylpyridine obtained by chlorination of β-picoline in the vapor phase can be increased by conducting the chlorination in the presence of a catalyst. The present invention concerns an improved process for chlorinating β-picoline (I)

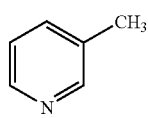

in the vapor phase at elevated temperatures to obtain a chlorination mixture enriched in 2-chloro-5-trichloromethylpyridine (β-2-tet) (II)

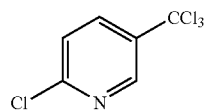

wherein the improvement comprises contacting the β-picoline (I) with chlorine in the presence of a dealuminated Mordenite zeolite or a supported palladium catalyst.

DETAILED DESCRIPTION OF THE INVENTION

In carrying out the present invention, β-picoline and chlorine are contacted in the vapor phase under conditions conducive to tetrachlorination in the presence of a dealuminated Mordenite zeolite or a supported palladium catalyst. A mixture containing as the primary product β-2-tet along with varying amounts of other polychloro-β-picolines is obtained.

In carrying out the present invention, vapors of β-picoline are mixed with an excess over the stoichiometric amount of gaseous chlorine during a brief contact time in the presence of a Mordenite zeolite or a supported palladium catalyst at a temperature of at least 175 to about 400° C. Alternatively, mixed vapors of β-picoline and an appropriate diluent are mixed with an excess over the stoichiometric amount of gaseous chlorine during a brief contact time in the presence of a Mordenite zeolite or a supported palladium catalyst at a temperature of at least 175 to about 400° C.

The amount of excess chlorine above the stoichiometric is not critical and may vary from stoichiometric to excess chlorine exceeding 400 moles chlorine per mole of β-picoline in the feed. Preferably the amount of excess chlorine above the stoichiometric will be at least 20 moles chlorine per mole β-picoline in the feed.

Diluents suitable for carrying out the process of the present invention are materials substantially inert to the action of chlorine under the reaction conditions and include nitrogen, argon, carbon dioxide, perfluorocarbons, perchlorocarbons and perfluorochlorocarbons. Preferred diluents are nitrogen and volatile perchlorohydrocarbons such as carbon tetrachloride and perchloroethylene. Suitable mole ratios of diluent to β-picoline may vary from about 10:1 to about 300:1.

The vapor phase reaction is conducted at a temperature range from about 175 to about 400° C. The preferred range is from about 250 to about 350° C.

Although residence time is not critical, the reactants should not be allowed to remain in contact with the catalyst for a prolonged period. Residence times generally will not exceed 60 seconds. The preferred time for contact is from about 0.5 to about 15 seconds at temperatures from about 250 to about 350° C.

Operating pressures are not critical and may vary from subatmospheric to superatmospheric. Atmospheric pressure is satisfactory and preferred. Elevated pressures may increase the reaction rates beneficially.

The zeolite family of Mordenite catalysts used in the present invention is well known to those skilled in the art. In general, the Mordenite catalyst is in the acid or H form (such as the HSZ-690HOD catalyst obtained from TOSOH Corporation of Japan with a SAR of 203). It is dealuminated according to procedures well known in the art, for example, by treating the catalyst with mineral acids (or amines, amine salts or organic acids) followed by calcination, to remove some of the alumina and to replace alkali metals with hydrogen (H form). (See Alan Dyer, "An introduction to Zeolite Molecular Sieves", John Wiley & Sons Editor, pg 113-115, New York (1988).) Catalysts with an SAR of 175 to 250 are preferred because they are resitant to acidic conditions and provide good yield of the desired product.

The supported palladium catalysts used in the present invention are also well known to those skilled in the art. In general, palladium can be supported on silica, alumina, magnesia or carbon with alumina being preferred. The catalysts range from about 0.1 to about 10 percent by weight palladium with about 0.5 to about 1.0 percent palladium being preferred.

The catalysts of the present invention may be bound in various forms with the aid of a binder. There are numerous types of binder available, examples include but are not limited to clays, amorphous silicas and aluminas. The process of forming a bound material is well known to those skilled in the art. Binder loadings are typically less than 30 wt % and preferably less than 20 wt %. The bound catalyst pellets can be of various sizes or shapes. The pellet shape or size is not critical. A typical shape would be cylinders ranging from 1/16 inch (1.59 millimeters (mm)) to 3/8 inch (9.53 mm) diameter and lengths ranging from less than half the pellet diameter to 20 times the pellet diameter. Alternative pellet shapes like spheres, tubes, saddles or lobed pellets are all suitable forms.

Any suitable reactor may be employed. The inlets and outlets as well as the interior surfaces of the reactor must be of materials such as are known to resist corrosion by chlorine and hydrogen chloride at high temperatures. Thus for example, exposed surfaces may be lined with or constructed of nickel, carbon, silica or glass. In practice, it has been found that thermally resistant, high-silica glass, such as Vycor brand, or quartz is satisfactory for small reactors. In large scale apparatus, it is convenient to use a shell of nickel lined with fused silica or a suitable refractory such as carbon. An unlined nickel or nickel alloy reactor is also suitable. To accomplish mixing and introduction of the reactants, the reactor may be fitted with a mixing nozzle for introducing the reactants with substantially simultaneous mixing. Alternatively, the β-picoline plus diluent and the chlorine may be introduced into the reactor by separate but closely spaced orifaces adjusted so that the chlorine is jetted into the incoming stream of β-picoline plus diluent. The reactor needs to be partially or substantially filled with the catalyst. Suitable reactor configurations for the reactor include shell and tube reactors, open pipes or fluidized bed reactors. For shell and tube style reactors the catalyst can be placed in either the tube or shell side. This can conveniently allow for control of the reaction temperature by circulation of a heat transfer fluid through the opposite side of the reactor. The proportions for the reactor are not critical. In a preferred form of apparatus, the reactor proper is in the form of a cylinder having a length of 1 to 30 times the diameter. The reactor is partially loaded with catalyst. Conventional accessories such as flowmeters, condensers and scrubbers are also employed.

In carrying out the reaction, β-picoline plus optionally a diluent are typically introduced into an evaporator to produce vaporized β-picoline in an inert diluent vapor. Alternatively chlorine gas can be used in the evaporator to produce a vaporized stream with the desired mixture of β-picoline and chlorine. The evaporator is maintained at a temperture at which rapid vaporization occurs, usually in the range from about 80 to about 250° C., preferably from about 100 to about 200° C. Any vaporizing device may be employed as an evaporator but, for larger scale, a wiped or falling film evaporator is convenient. For efficient operation, it is necessary that the rate of introduction of β-picoline and/or the temperature of the evaporator be maintained so as to completely vaporize the β-picoline and to keep it in the vapor state. The mixed vapors from the evaporator are conducted to the reactor where they are contacted with chlorine at a temperature from about 175 to about 400° C., preferably from about 250 to about 350° C., in the presence of the dealuminated Mordenite zeolite or the supported palladium catalyst. The vapors passing through the reactor are cooled or quenched to separate the chlorinated picoline products from the gaseous chlorine and by-product hydrogen chloride. The desired β-2-tet is separated from the other chlorinated picoline products by conventional techniques such as fractional distillation. Any under-chlorinated picoline products can be separated from the β-2-tet and recycled to the reactor. In small scale equipment the reactor exit gases can be characterized using gas chromatography.

The following examples illustrate the invention.

EXAMPLES

Reactor Set-Up for Experiments

An oven capable of sustainable temperatures up to 400° C. was fitted with three independent reactor systems. The reactors consisted of a 5 inch (") (12.7 centimeters (cm)) long, rod-shaped, Pyrex glass tube with 0.25" (6.35 mm) OD. The reactor tubes were either empty (used for control) or packed with a catalyst with the bed ranging from 0.25 grams (g) to 0.5 g in weight and about 30 to 75 mm in length depending upon catalyst density and the weight of catalyst used. The catalyst and catalyst support systems were typically taken from larger pellets that were commercially available and ground and sized using screens to approximately 1-2 mm in diameter. Heated feed (and exit) lines to (and from) the reactors were typically made out of nickel or Inconel 600 and were kept at temperatures known in the art to avoid the condensation or degradation of reactants and products therein.

Chlorine was fed into each individual reactor system independently. The chlorine was controlled by separate 3-way valves and a mass-flow controller for each system. The 3-way valve controled chlorine feeding into each reactor and allowed the feed line to be purged with nitrogen when not in use. The mass-flow controller controled the flow rate of chlorine in the system at set values, typically 5 standard cubic centimeters (sccm). Chlorine was typically the first gas to be fed to the reactor system prior to feeding organic vapors to the catalyst.

β-Picoline was fed into each reactor from separate evaporator units contained in a chiller bath capable of −20 to 120° C. temperatures. Nitrogen was used as the sweep gas through the evaporators. The evaporators were cylinder-shaped Pyrex reservouries that held the β-picoline below the nitrogen gas flow. The feed rate of nitrogen was typically kept at 10 sccm set by a mass-flow controller. The evaporators were set in the chiller bath below the liquid level. The chiller bath was typically operated at either 10 or 20° C., which gave β-picoline vapor pressures of 3.09 $E^{-3}$ atmospheres (atm) or 5.93 $E^{-3}$ atm respectively. The feed and the exits to the reactor systems were operated near or about atmospheric pressure.

The chlorine feed was mixed with β-picoline vapor inside the oven in a mixing tube before the reactor inlet. The mixture of the two reactants was then fed into the 5" long, 0.25" O.D. rod-shaped, Pyrex glass reactor. The product streams from the reactors were directed to an 8-port valve and then selectively sent to either the online analysis system, or to the scrubber system through an organic trap and the venting system. The reactor was then fed chlorine followed by the β-picoline in nitrogen. Catalyst conditioning could be achieved by starting the reaction at a temperature of 250° C. then slowly increasing to the reaction temperature in 25 to 50° C. increments over a finite period of time. The on-line analysis system consisted of gas chromatography (GC) and mass spectral (MS) analysis. The GC capillary column used was an RXT-5, 15 m×0.530 mm, 1.50 μm film thickness. The oven temperatures were programmed to give maximum separation in a minimum time. The cycle time for the GC analysis was about 15 minutes and the GC analysis was calibrated using standard samples. The analysis was taken at regular intervals of approximately 15 to 60 minutes and the values reported are given in weight percent once the system had stabilized at the desired reaction condition settings.

The software used for process controls for the micro-reactor system was Camile TG. The Camile TG monitored the pressure inside each reactor system, and controled the temperatures for ovens, vent lines, and the chiller bath and the mass-flow controllers for nitrogen and chlorine feeds. The reactor oven temperature was controlled by Camile operating under macro programs with temperature profiles between the range of 200° C. and 400° C. The vent lines and the analytical transfer lines from the valve box were heat traced and are kept at elevated temperature to insure the contents were in the gas phase.

Example 1

The pelletized catalyst, 0.5% palladium catalyst on alumina (Harshaw Chemical Co.), was ground to a coarse powder and screened to obtain a uniform size of 1-2 mm in diameter. A weight of 0.25 g of catalyst was charged into the 0.25" reactor tube and glass wool (Pyrex) was used to secure it in place. Operating at an initial temperature of 250° C., a chlorine feed of 5 cc/min, a β-picoline feed rate of 0.13 mg/min (10 cc/min $N_2$ with a chiller temperature of 10° C.), the reactor was ramped up to 340° C. over about one hour. After the system stabilized at the reaction temperature of 340° C., the product gases contained 67.4% β-2-tet (see Table 1 for conditions and Table 2 for results).

Example 2

The pelletized catalyst, TOSOH HSZ-690 HOD (SAR 203) with a silica binder, was ground to a coarse powder and screened to obtain a uniform size of 1-2 mm in diameter. A weight of 0.26 g of catalyst was charged into the reactor tube and glass wool (Pyrex) was used to secure it in place. Operating at a chlorine feed of 5 cc/min, a β-picoline feed rate of 0.13 mg/min (10 cc/min $N_2$ with a chiller temperature of 10° C.), the reagents were fed to the reactor at an initial temperature of 250° C. The system was initially ramped up to 325° C. and allowed to stablize. Under these conditions the product gases were 18.5% 3-trichloromethylpyridine (β-tri ) and 65.4% β-2-tet. When the system was allowed to stabilized at 350° C. the amount of β-tri in the product gases was reduced to 2.6% and the conversion to β-2-tet increased to 68.6% (see Table 2).

Example 3

The catalyst, TOSOH HSZ-690 HOD (SAR 203) with the silica binder, was sized to a uniform particle size of 1-2 mm in diameter. A weight of 0.26 g of catalyst was charged into the reactor tube and glass wool (Pyrex) was used to secure it in place. The reactor temperature was initially set to 250° C. prior to flowing chlorine at a rate of 5 cc/min. The β-picoline feed rate was set to 0.13 mg/min ($N_2$ flow 10 cc/min, chiller at 10° C.), while the reactor oven was ramped up to 350° C. over a one hour time period. At 350° C. the amount of β-2-tet observed in the product gases was 65.6% (see Table 2).

Example 4

The catalyst, TOSOH HSZ-690 HOD (SAR 203) with the silica binder, was sized to a uniform particle size of 1-2 mm in diameter. A weight of 0.51 g of catalyst was charged into the reactor tube and glass wool (Pyrex) was used to secure it in place. The reactor temperature was initially set to 250° C. prior to flowing chlorine at a rate of 5 cc/min. The β-picoline feed rate was set to 0.13 mg/min (chiller at 10° C.), with a nitrogen flow of 10 cc/min, while the reactor oven was ramped up to 350° C. over 2 hours. When the system had stabilized at 350° C. the amount of β-2-tet observed in the product gases was 71.7% (see Table 2).

Example 5

The catalyst, TOSOH HSZ-690 HOD (SAR 203) with the silica binder, was sized to a uniform particle size of 1-2 mm. A weight of 0.51 g of catalyst was charged into the reactor tube and glass wool (Pyrex) was used to secure it in place. The reactor temperature was initially set to 250° C. prior to flowing chlorine at a rate of 5 cc/min. The β-picoline feed rate was set to 0.25 mg/min ($N_2$ at 10 cc/min, chiller at 20° C.), while the reactor oven was slowly ramped up to 350° C. over 2 hours. When the system had stabilized at 350° C. the amount of β-2-tet observed in the product gases was 66.9% (see Table 2).

Example A

This is the control run where the reactor contained glass wool (Pyrex) plugs and no catalyst. The reactor temperature was initially set to 350° C. prior to feeding chlorine at a rate of 5 cc/min. The β-picoline feed rate was set to 0.25 mg/min ($N_2$ at 10 cc/min, chiller at 20° C.) at the oven temperature of 350° C. When the system had stabilized the amount of β-2-tet was only 8.7%, with the majority of the conversion going to β-tri (65.4%). When the temperature was increased to 400° C. the amount of β-2-tet increased to 46.1% with a reduction in β-tri (21.5%). A fair amount of over chlorinated 2,6-dichloro-3-trichloromethylpyridine (β-2,6-penta,12.2%) was also observed (see Table 2).

TABLE 1

EXPERIMENTAL CONDITIONS FOR EXAMPLES

| Ex. No. | Catalyst | Source | Binder | Cat. wt (g) | Metal | Temp °C. | Picoline Feed Rate mg/min |
|---|---|---|---|---|---|---|---|
| 1 | Pd on Alumina 0.5% | Harshaw | $Al_2O_3$ | 0.25 | Pd | 340 | 0.13 |
| 2 | HSZ-690HOD SAR 203 | Tosoh | $SiO_2$ | 0.51 | none | 350 | 0.13 |
| 3 | HSZ-690HOD SAR 203 | Tosoh | $SiO_2$ | 0.26 | none | 350 | 0.13 |
| 4 | HSZ-690HOD SAR 203 | Tosoh | $SiO_2$ | 0.51 | none | 350 | 0.13 |
| 5 | HSZ-690HOD SAR 203 | Tosoh | $SiO_2$ | 0.51 | none | 350 | 0.25 |
| A | Empty Tube | — | none | none | none | 400 | 0.25 |

TABLE 2

TABULATED GC RESULTS FOR EXAMPLES
GC Normalized Weight Percent Analysis

| Ex. No. | DCP | TCP | β-Tri | 2C-3DCM | 2C-5DCM | β-2-Tet | β-6-Tet | β-2,3-Penta | β-2,6-Penta |
|---|---|---|---|---|---|---|---|---|---|
| 1 | 1.4 | 0.0 | 7.2 | 8.8 | 1.0 | 67.4 | 6.6 | 0.0 | 4.7 |
| 2 | 0.0 | 0.4 | 2.6 | 3.0 | 0.0 | 68.6 | 7.8 | 5.0 | 6.1 |
| 3 | 0.0 | 0.0 | 16.5 | 6.9 | 0.0 | 65.6 | 5.4 | 1.1 | 3.5 |
| 4 | 0.0 | 0.0 | 4.8 | 5.3 | 0.0 | 71.7 | 6.1 | 3.2 | 4.4 |
| 5 | 0.0 | 0.0 | 12.0 | 7.0 | 0.0 | 66.9 | 5.3 | 0.8 | 4.1 |
| A | 0.0 | 2.7 | 21.5 | 2.3 | 0.0 | 46.1 | 8.4 | 0.6 | 12.2 |

Note:
DCP = Dichloropyridine isomers;
TCP = Trichloropyridine isomers;
β-Tri = 3-trichloromethylpyridine;
2C-3DCM = 2-Chloro-3-dichloromethylpyridine;
2C-5DCM = 2-chloro-5-dichloromethylpyridine;
β-2-Tet = 2-chloro-5-trichloromethyl-pyridine;
β-6-Tet = 2-chloro-3-trichloromethylpyridine;
β-2,3-Penta = 2,3-dichloro-5-trichloromethylpyridine;
β-2,6-Penta = 2,6-dichloro-3-trichloromethylpyridine

What is claimed is:

1. An improved process for chlorinating β-picoline (I)

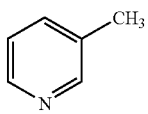

in the vapor phase at elevated temperatures to obtain a chlorination mixture enriched in 2-chloro-5-trichloromethylpyridine (β-2-tet) (II)

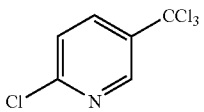

wherein the improvement comprises contacting the β-picoline (I) with chlorine in the presence of a dealuminated Mordenite zeolite or a supported palladium catalyst.

2. A process according to claim 1 in which the β-picoline is contacted with chlorine in the presence of a dealuminated Mordenite zeolite catalyst.

3. A process according to claim 1 in which the β-picoline is contacted with chlorine in the presence of a supported palladium catalyst.

* * * * *